(12) United States Patent
Kim et al.

(10) Patent No.: US 7,247,501 B2
(45) Date of Patent: Jul. 24, 2007

(54) IMAGING AND TARGETING TUMORS USING SICKLE CELLS

(75) Inventors: Jae Ho Kim, West Bloomfield, MI (US); Stephen Lawrence Brown, LaSalle (CA); Paul S. Swerdlow, Farmington Hills, MI (US)

(73) Assignees: Henry Ford Health System, Detroit, MI (US); Wayne State University, Detroit, MI (US)

( * ) Notice: Subject to any disclaimer, the term of this patent is extended or adjusted under 35 U.S.C. 154(b) by 305 days.

(21) Appl. No.: 10/311,261

(22) PCT Filed: Jun. 22, 2001

(86) PCT No.: PCT/US01/19846

§ 371 (c)(1),
(2), (4) Date: Jul. 1, 2003

(87) PCT Pub. No.: WO01/97678

PCT Pub. Date: Dec. 27, 2001

(65) Prior Publication Data

US 2004/0057940 A1    Mar. 25, 2004

Related U.S. Application Data

(60) Provisional application No. 60/213,516, filed on Jun. 22, 2000.

(51) Int. Cl.
*G01N 33/555* (2006.01)
*A61K 51/00* (2006.01)

(52) U.S. Cl. ................... 436/520; 424/1.17
(58) Field of Classification Search ............... None
See application file for complete search history.

(56) References Cited

U.S. PATENT DOCUMENTS 5,939,456 A    8/1999 Perrine
6,011,000 A    1/2000 Perrine et al.
6,197,278 B1   3/2001 Blankenberg et al.
6,231,880 B1   5/2001 Perrine

OTHER PUBLICATIONS

Fabry et al (Proc. Nat. Acad. Sci. USA 86: 3308-3812, 1989).*
Verma et al (Nature 389: 239-242, 1997).*
Anderson (Nature 392:25-30, 1998).*
Romano et al (Stem Cells 18: 19-39, 2000).*
Somia and Verma (Nature Reviews Genetics 1: 91-99, 2000).*
Orkin and Motulsky (Report and Recommendations of the Panel to Assess the NIH Investment in Research on Gene Therapy, p. 1-38, Dec. 7, 1995.*
Ehrenreich et al (Cleveland Clinic journal of medicine, (Mar.-Apr. 1995) 62 (2) 105-16).*
Tzeng et al (Journal of pharmacokinetics and biopharmaceutics, (Jun. 1992) 20 (3) 227-51)).*
Al-Ali (Acta Haem. 108: 19-22, 2002).*
Kruise et al (Biotechnology and Applied Biochemistry 9(2):123-140, 1987).*
Slavin et al (Brit. J. Surg. 79(9): 918-921, 1992).*

* cited by examiner

*Primary Examiner*—Richard Schnizer
(74) *Attorney, Agent, or Firm*—Kenneth I. Kohn; Kohn & Associates, PLLC

(57) ABSTRACT

According to the present invention, there is provided a delivery vehicle including sickle red blood cells carrying a moiety. The moiety can be any type of diagnostic or therapeutic agent. The present invention further provides for a method of diagnosing systemic hypoxia, acidosis, or hypertonicity by administering sickle red blood cells to a patient and detecting the location of the sickle red blood cells. Additionally, the present invention provides for a method of therapeutic treatment of systemic hypoxia, acidosis, or hypertonicity by administering sickle red blood cells to a patient. Further, the present invention provides for a delivery vehicle that specifically localizes or concentrates at systemic hypoxia, acidosis, or hypertonicity areas. The delivery vehicle is used in diagnosing and therapeutically treating these areas of hypoxia, acidosis, or hypertonicity also. The present invention further provides for a method of making the delivery vehicle described herein.

7 Claims, 3 Drawing Sheets

IMAGING AND TARGETING TUMORS USING SICKLE CELLS

CROSS-REFERENCE TO RELATED APPLICATION

This patent application is a National Phase Concerning a Filing Under 35 U.S.C. 371, claiming the benefit of priority of PCT/US01/19846, filed Jun. 22, 2001, which claims the benefit of priority of U.S. Provisional Application Ser. No. 60/213,516 filed Jun. 22, 2000, all of which are incorporated herein by reference.

BACKGROUND OF THE INVENTION

1. Field of the Invention

This invention generally relates to the field of delivery vehicles for use in diagnostic and therapeutic applications, and specifically towards diagnostic and therapeutic applications involving hypoxic areas of a patient.

2. Description of Related Art

Hypoxic tissue areas are defined as areas having low oxygen content. Generally, the hypoxic tissue area is a result of numerous factors including, but not limited to, a reduction of the oxygen-carrying capacity of blood as a result of a decrease in the total hemoglobin or an alteration of the hemoglobin constituents, decreased blood flow, and any abnormal cellular growth. As a result of the decreased oxygen content, the hypoxic areas are further characterized as having increased tonicity, and a low pH due to acid build-up resulting from anaerobic glycolosis.

Hypoxic areas occur anywhere in the body of a patient, but are particularly found in areas associated with injuries occurring as a result of a stroke, decreased blood flow, reperfusion injury, decreased vascular development, and tumors. With regard to tumors, experiments have provided direct and indirect evidence of hypoxic areas occurring in tumors therein. For example, tests involving glass polarographic electrodes confirm the presence of hypoxia in tumors.

Hypoxic areas located within regions of a tumor are of particular concern to researchers involved with tumor and cancer treatment. Low oxygen levels within regions of a tumor or cancer limits the effectiveness of radiation therapy, since cells maintained in a hypoxic environment are resistant to radiation damage. Radiation resistance occurs because free radicals produced in the presence of low oxygen levels are less damaging toward tumor cells. Consequently, more treatment is required in these hypoxic areas in order to kill the tumor cells.

Generally, in order to treat tumors, the tumor regions must first be found and then targeted. Presently, there is no routine technique available to target tumor tissue. More importantly, no routine clinical tool is available specifically applicable towards imaging tumor hypoxia and to deliver treatment directly thereto.

A number of techniques to monitor tumor hypoxia are available or are under development. These techniques include glass polarographic assay, alkaline comet assay, nitroimidizole-related radiolabelled compounds (Zhang et al. 1998), and fluorine-MRI using hexofluorobenzene. The most widely used measurement of tumor hypoxia is the glass electrode technique. The limitations of this technique however, are that measurements do not adequately represent the entire tumor, since measurements are limited to tissue oxygenation along a linear tract, 1 or 2 mm deep.

Other techniques for measuring tumor hypoxia include NMR of fluorinated compounds (Mason et al. 1998) and techniques based on oxygen quenching of the fluorescence of an excited fluorophor immobilized in a polymer at the end of an optical fiber (Young et al. 1996). The inherent problem with these techniques is that they all require tumor access and are highly invasive. On the other hand, techniques that are non-invasive, such as imaging techniques using nitroimidazole analogues, yield only relative values of tissue oxygen since binding intensity is affected by tumor metabolism.

Accordingly, there is a need for a non-invasive, accurate and detectable mechanism for determining the location of hypoxic areas, and specifically hypoxic areas associated with tumors. Moreover, there is a need for a method of diagnosing and therapeutically treating hypoxic areas associated with tumors. Additionally, there is a need for a routine, non-invasive measurement of human tumor hypoxia in order to determine the effectiveness of chemotherapy as well as radiation therapy. Further, there is a need for improving standard radiation therapy by targeting the small radiation resistant hypoxic regions of a tumor.

SUMMARY OF THE INVENTION

According to the present invention, there is provided a delivery vehicle including sickle red blood cells carrying a moiety. The moiety can be any type of diagnostic or therapeutic agent. The present invention further provides for a method of diagnosing systemic hypoxia, acidosis, or hypertonicity by administering sickle red blood cells to a patient and detecting the location of the sickle red blood cells. Additionally, the present invention provides for a method of therapeutic treatment of systemic hypoxia, acidosis, or hypertonicity by administering sickle red blood cells to a patient. Further, the present invention provides for a delivery vehicle that specifically localizes or concentrates at systemic hypoxia, acidosis, or hypertonicity areas. The delivery vehicle is used in diagnosing and therapeutically treating these areas of hypoxia, acidosis, or hypertonicity also. The present invention further provides for a method of making the delivery vehicle described herein.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
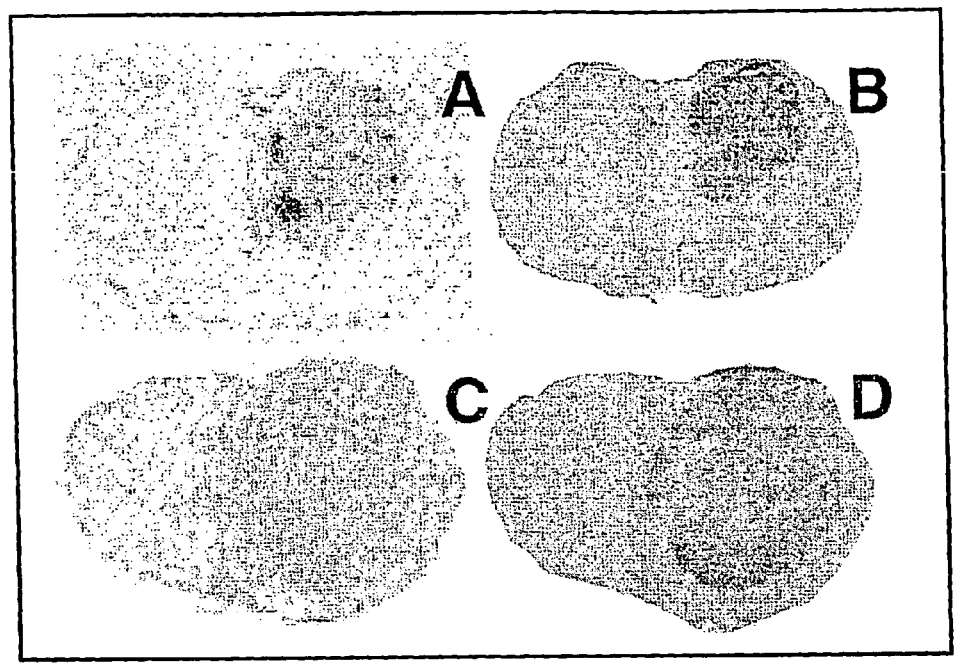
FIG. 1 illustrates results from a brain autoradiography and histopathology of adjacent slices in 17 day old intracranial 9L rat tumors where, Panel A is an autoradiographic section (20 μm thick) 1 hour after intravenous administration of human sickle RBCs labeled with Tc-99m, Panel B illustrates the adjacent hematoxylin and eosin, H&E, stained section (10 μm thick) where the intense dark region represents tumor, Panel C demonstrates autoradiography 1 hour after intravenous administration of normal human RBCs labeled with Tc-99m, Panel D illustrates the adjacent H&E stained section.

The present invention provides for a delivery vehicle that delivers a specific moiety to areas of a patient's body. Preferably, the delivery vehicle is a sickle red blood cell carrying the specific moiety and the moiety is any type of therapeutic or diagnostic compound or substance, but is preferably a diagnostic agent, therapeutic agent, or combinations thereof. The sickle red blood cells used include, but are not limited to, sickle cell anemia cells, sickle-hemoglobin C disease cells, sickle thalassemia cells (beta 0 or beta +), sickle globin cells, sickle mutation cells such as Hb S Antilles, and any similar cells known to those of skill in the art. Basically, any cell having hemoglobin molecules that polymerise in response to hypoxia, acidosis, or altered tonicity can be utilized with the present invention. Additionally, the delivery vehicle includes, but is not limited to, other types of cells, micelles, vesicles, microvesicles, and any other similar particles or structures that can localize, accumulate, and/or concentrate in areas of specific physiology such as hypoxia, acidosis, and hypertonicity.

The present invention is well suited for delivery of substances and compounds to specific areas of a patient's body. The present invention is capable of targeting any area of the body or towards specific organ and tissue regions. The specific tissue regions include, but are not limited to, areas of hypoxia, acidosis, altered tonicity (hypertoncity), and any other similar areas that can be targeted with the present invention and known to those of skill in the art. Thus, the present invention can be a carrier for a substance or compound, or the delivery vehicle itself can be used for diagnosing and/or therapeutically treating any disease, illness, or other similar targeted area.

The various substances and compounds are bound within delivery vehicle of the present invention or to the outer membrane of the vehicle. The substances and compounds can be released or localized at the targeted site, remain inside the vehicle, or remained attached to the vehicle. For example, radioisotopes can remain within the vehicle such that effective treatment is provided in the localized hypoxic area of a tumor. The substances and compounds thus can be chemically bound to the vehicle through methods and mechanisms known to those of skill in the art. Additionally, any number of vehicles can be used, depending upon the amount of substances and compounds desired to be delivered and localized.

There are numerous uses for the present invention. The present invention is useful in delivering or localizing any substance or compound, including, but not limited to, diagnostic agents, therapeutic agents, pharmaceutical compounds, combinations thereof, and any other similar substance or compound known to those of skill in the art. Thus, the present invention is useful in both the diagnosis and therapeutic treatment of any disease or illness. Additionally, the present invention can interact synergistically with other agents involved with radiation, chemotherapy, heat, inflammatory protectors, and the like, either to enhance tumor cytotoxicity or to protect normal tissues.

As for the diagnostic agents, the present invention delivers agents including, but not limited to, image contrasting agents, isotopes, radioactive labels, immunofluorescent tags, Gd, Gd-DTPA, antibodies, drugs, compounds, proteins, pharmaceutical compositions, and any similar agents or compounds known to those of skill in the art.

As for the therapeutic agents, the present invention delivers agents including, but not limited to, isotopes, radioisotopes, radionuclides, chemotherapy, antibodies, anti-inflammatory agents, metabolites such as Cordox, fructose diphosphate and oxygen, reperfusion injury-affecting agents, angiogenic factors, angiogenic promoters, anti-tumor agents, cytostatic agents for chemotherapy, radiosensitizers, gene vectors, vascular tone-affecting agents such as compounds, pharmaceuticals, drugs, adjuvants, and any other similar therapeutic agents known to those of skill in the art.

In addition to delivering agents, the present invention has numerous other uses and applications. For instance, the present invention is capable of imaging hypoxic areas of tumors, acidosis areas, hypertoncitiy areas, and other pathologic states related to stroke or vascular obstruction. Other uses include, but are not limited to, decreasing blood flow to certain areas of the body or to certain organs and tissues, assessing tumor oxygen status, assessing tumor acidity, assessing tumor tonicity, detecting peripheral vascular disease, improving vascular development, studying sickling in patients with sickle cell anemia, angiogenesis, decreasing reperfusion injury, and any other similar applications known to those of skill in the art.

The present invention is useful in numerous environments. The present invention is used in various subjects and patients including, but not limited to, in vivo applications involving animals and humans, and in vitro applications involving animal and human cells, and any other application known to those of skill in the art.

In the preferred embodiment, the present invention utilizes sickle red blood cells as the delivery vehicle of the moieties previously described herein. Sickle red blood cells occur in those having sickle cell anemia, which is a disease characterized by red blood cell coagulation. Sickle red blood cells become sickle shaped in a low oxygen environment, aggregate, and then obstruct the flow of normal circulation. Sickle cell hemoglobin preferentially precipitates out of solution under hypoxia (typically<27 mmHg for >30 s) and acidic conditions. The insoluble hemoglobin forms long polymers that distort the shape and change the flexibility of the red blood cells, which then can obstruct blood flow.

The tumor microenvironment is uniquely suited to precipitate such "sickling." Tumors are characterized by regions of low oxygen tension and low pH. Both conditions enhance sickle hemoglobin polymerization. Tumor microvessels promote sickle cell accumulation due to their tortuous chaotic architecture and abnormal vessel lining. Furthermore, the low blood flow is likely to cause the cells to remain in hypoxic areas longer than their delay time, further localizing sickle cells to the tumor microvasculature. As a result, sickle red blood cells reliably and preferentially aggregate in hypoxic tumor vasculature.

These same hypoxic regions are acidic because hypoxic tumor cells utilize anaerobic glycolosis for their energy supply, a by-product of which is lactic acid. Therefore, regions of tumor are characterized by low oxygen, high acidity, two conditions that precipitate the sickling phenotype. Furthermore, tumor regions with sluggish, tortuous blood flow facilitate sickle cell coagulation. Thus, hypoxia is one of the primary impetuses for expression of the sickle cell phenotype.

The present invention utilizes the properties and characteristics of sickle red blood cells in hypoxic areas in order to locate these areas. In one embodiment of the present invention, hypoxic areas are imaged using sickle red blood cells and functional magnetic resonance imaging so that the regions are targeted with ionizing radiation to improve the effectiveness of cancer control. As previously discussed, hypoxic tumor regions account for radiation resistance and are considered a clinical impediment to effective radiation therapy. Cancer cells in a low oxygen environment require two to three times the radiation dose to achieve a level of killing.

In the preferred embodiment, the sickle red blood cells can be modified in any manner in order to practice the present invention. Blood type specific sickle red blood cells are used in accordance with each individual patient. Methods known to those of skill in the art are used to load any agent into the cell or onto the surface of the cell. Subsequently, the sickle red blood cells can then be administered to the patient intraveneously, infused directly into arteries feeding the pathologic areas, or through any similar injecting technique known to those of skill in the art.

Once the loaded sickle red blood cells reach the targeted area, the agents can be slowly released from the sickle red blood cells. A slow release of cytotoxic compounds from cells increases efficacy of treatment. Thus, agents such as 5-FU, a widely used chemotherapeutic agent, can be loaded into a sickle red blood cell and be slowly released at the tumor site. This has been demonstrated using 9L cells and 5-FU, wherein the sickle red cells loaded with 5-FU are lysed in contact with 9L cells. As a result, the 9L cell survival was reduced to 10% of its original survival. However, when sickle red blood cells are loaded with 5-FU and not lysed, the survival of 9L cells in contact is reduced to less than 1% of the original level of survival.

In operation, the present invention is used in diagnostic and therapeutic applications with regard to hypoxic areas. In order to diagnose the presence of hypoxic areas, the present invention utilizes sickle red blood cells and subsequent diagnostic techniques. The diagnostic techniques include, but are not limited to, magnetic resonance imaging, autoradiography, nuclear medicine imaging, laser scanning confocal microscopy, nuclear magnetic resonance imaging (also known as Blood Oxygen Level Dependent Imaging or Functional MRI), hypoxia probing, using glass electrodes, spectral analysis of reflected or transmitted light (Pulse-Ox), and any other similar techniques known to those of skill in the art. Some of these methods are described hereinafter, and are also illustrated in the following examples.

The use of MRI to non-invasively diagnose and detect tumor hypoxia is novel and allows for high resolution and short acquisition times. Additionally, the present invention provides for the elucidation of the tumor microenvironment parameters leading to preferential sickle cell congestion.

In comparison with other techniques, magnetic resonance imaging (MRI) has many potential advantages, including high spatial resolution, the ability to image, and non-invasiveness. In another embodiment of the present invention, detection occurs through the use of functional MRI or Blood Oxygen Level Dependent imaging (BOLD-MRI). BOLD-MRI relies on hemoglobin from intact red blood cells as an imaging contrast agent to detect changes in oxygen using differences in the magnetic properties of oxyhemoglobin and deoxyhemoglobin. The technique requires a change in tissue oxygen to produce signal contrast, typically by breathing gas mixtures with more oxygen than air. The detection of tissue hypoxia by BOLD-MRI is improved through the use of a localized contrast agent that becomes paramagnetic in hypoxic regions, since the large signal decrease is apparent in the image independent of other physiological effects. BOLD-MRI enables the detection of low oxygen tumor microregions in three-dimensions at sub-millimeter in-plane resolution.

Through BOLD-MRI, sickle red blood cells are ideal imaging contrast agents for diagnosing tumor hypoxia. First, sickle red blood cells are unusual in that they distort and aggregate in regions of hypoxia. The low oxygen tension and high acidity environment of hypoxic regions enhance the distortion of sickle red blood cells. Second, sickle red blood cells adhere to blood vessel walls, especially in damaged vasculature. Tumor vasculature in regions of tumor hypoxia is inferior and abnormal and thus cause sickling. Third, sickle red blood cells must be exposed to appropriate conditions of hypoxia and acidity for an extended period of time, typically 30 seconds, to precipitate sickling. The transit time of red blood cells through hypoxic tumor regions is increased compared with that of normal tissue due to sluggish tumor blood flow and tortuous, chaotic tumor vasculature. In summary, the red blood cells from patients with sickle cell anemia are well suited to aggregate in hypoxic tumor vasculature. Sickle red blood cells are a well suited contrast agent of tumor hypoxia for BOLD-MRI because sickle red blood cells are in a deoxyhemoglobin state, and deoxyhemoglobin is paramagnetic.

A T2-weighted gradient echo sequence was used for functional MRI experiments or BOLD-MRI, a pulse sequence which derives its contrast from deoxygenated hemoglobin. The sequence allows for multi-slice gradient-echo image acquisition in short time periods, 1 s. Imaging parameters are 64×64 matrix, FOV=32 mm, TE/TR=30/15 ms, three contiguous slices, slice thickness=22 mm, flip angle θ=25°. Images are acquired in groups of 40, before the infusion of red blood cells and multiple times after the administration of red cells. A significant decrease in signal in a localized area encompassing several pixels is interpreted as sickle cell aggregation. The 40 pre-blood images are compared to the post-blood signal intensity on a pixel-by-pixel basis and using a t-test comparison with a level of significance, $p<0.01$ two-tailed. A processed image is created that maps pixels that significantly decrease after sickle blood administration. The signal intensity in the processed image is linearly related to the magnitude of the change in signal intensity from the pre-blood image, so regions of red cell accumulation are evident. Deoxyhemoglobin accumulates in specific tumor areas following the administration of sickle red blood cells (number of rats, n=3). No accumulation occurs in normal tissue (n=3) and no accumulation occurs in tumors under two control conditions: administration of normal human blood, n=1, and administration of sickle red blood cells during carbogen breathing, n=1.

EXAMPLES

In the following examples, red blood cells from patients with sickle cell anemia are shown to preferentially aggregate in tumor regions using cells labeled with fluorescence, radioactivity, or loaded with Gd-DTPA. In all cases, control cells from normal patients do not show statistically significant preferential aggregation in tumor tissue.

Various techniques are utilized to demonstrate the preferential aggregation of sickle red blood cells in tumor regions. For sickle red blood cells labeled with fluorescence, laser scanning confocal microscopy is used. For sickle red blood cells labeled with radioactivity, a nuclear medicine imaging or an autoradiography technique is utilized. Finally, sickle red blood cells loaded with Gd-DTPA are analyzed using nuclear magnetic resonance imaging. Additionally, through the use of functional magnetic resonance imaging, sickle red blood cells are shown to aggregate in tumor regions, particularly the hypoxic regions of the tumors.

General Experimental Techniques, Methods and Materials:

Tumor Types:

A variety of tumor types were used. One mouse tumor used, a mouse mammary carcinoma, is characterized by the presence of chronic hypoxia. The rat tumor used is the 9L glioma.

Transplantable mouse tumors are inoculated in the right hind leg muscle of host animals. Mouse tumors are used when they are large, at approximately 12 mm in diameter. The mouse mammary ca in C3H mice is obtained from Dr. H Stone (formerly at UCSF). It contains a sizable hypoxic fraction, 40%, in tumor volumes of 500 to 700 $mm^3$.

The 9L tumor model is a widely used rat brain tumor model, well characterized with respect to its radiation response and hypoxic fraction. obtained from Dr. Kenneth Wheeler, Wake Forest University, the tumor line was originally derived from rat brain. Cells are maintained by serial passage in vitro using Dulbeccos medium and 10% fetal calf serum. The rat's head is immobilized using a small animal stereostatic device. Following a midline incision, the skull is exposed. A burr hole is drilled through the skull taking care not to penetrate the dura. Ten thousand cells in 5 µl are injected at a rate of 1 µl/minute into a location 2.5 mm anterior to the bregma, 2.0 mm to the right of the midline and a depth of 3.0 mm, as described previously (Kim et al. 1995). Following stereostatic implantation, the tumor grows exponentially with a diameter doubling time of approximately three days. (Brown et al. 1999) The 9L tumor has a clearly defined border that is easily discernible using MRI. The radiobiological hypoxia fraction of 9L intracerebral tumors is less than about 3% (Leith et al. 1975, Moulder and Rockwell 1984, Wheeler and Wallen 1980).

Sickle Cells:

Human sickle cells are obtained from Barbara Ann Karmanos Cancer Institute approximately one day prior to an experiment and transported to Henry Ford Health System at room temperature using a Styrofoam thermos and stored at room temperature. Cells are washed at least twice prior to an experiment by mixing the blood sample, approximately 3 mls of blood, with 50 mls of isotonic saline and centrifuging the mixture for 10 minutes at 1000 rpm. Human red cells are mechanically compatible with a rat since capillary size is markedly constant across mammalian species, including rat and human with a mean diameter of 4 µm (Henquell et al. 1976, Sobin and Tremer 1972), and although normal human red cells have a slightly larger diameter than that of rat red cells (8.0 µm versus 7.5 µm under unstressed conditions, Smith et al. 1978), red cells of both species regularly traverse capillaries with diameters of 4 µm and even squeeze through endothelial slits that are only 0.5 to 1 µm wide.

Alternatively, mouse sickle cells are obtained from Meharry Medical College. Transgenic mice that express 100% S Antilles hemoglobin are used for the studies. The hemoglobin is 40% less soluble and 33% more easily deoxygenated.

Example One

Nuclear Medicine Imaging

Figure 3:
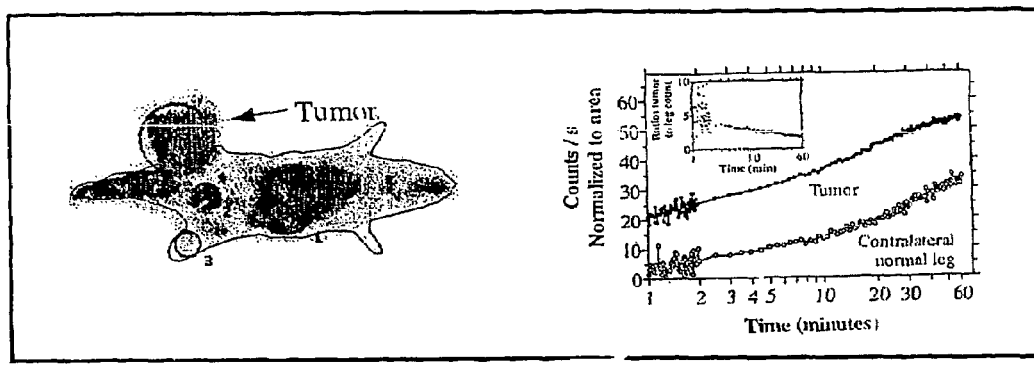
FIG. 3 illustrates the non-invasive imaging of radiolabled sickle cells, Panel 3a is a picture of a Fischer rat with a large 9L leg tumor where radiolabeled human sickle red blood cells were injected intravenously into the tail vein and four regions were monitored as a function of time: 1. Liver/spleen, 2. Bladder, 3. Contralateral normal leg, 4. Tumor, while Panel 3b is a chart demonstrating the radioactive counts per pixel per sec as a function of time in normal leg, region 3, and tumor, region 4, where images were obtained as 1s intervals for 2 min and at 30s intervals for the next 60 min. (counts were corrected for Tc-99m physical decay and inset shows ratio of tumor to leg counts as a function of time)

Radiolabeled sickle cells can be imaged relatively non-invasively using nuclear medicine imaging. FIG. 3 illustrates an example of the resulting image from a clinical scintillation scanner following the intravenous administration of human sickle cells to a rat with a large 9L tumor implanted in its right leg. Radioactivity increases sharply over the first several minutes and continues to increase more slowly over the next hour. The highest activity is found in regions of the rat corresponding to the tumor and some normal tissues, for example, the spleen or liver. Regions of interest are drawn around the liver, spleen, bladder, normal leg muscle, and tumor in order to monitor changes in radioactivity as a function of time. The results are shown in FIG. 3.

FIG. 3b demonstrates preferential accumulation of sickle cells in tumor immediately. Furthermore, the temporal data shown in FIG. 3b suggests that further accumulation in the tumor over the next hour is not preferential since tumor and contralateral normal muscle activity increase at the same rate. The data suggests that imaging should be performed early, within several minutes if injection, rather than later, for example at 1 hour.

Between 30 minutes and 1 hour after infusion, radioactive counts in the tumor are higher by approximately 2 times compared with contralateral normal leg muscle when human sickle cells are used. Larger tumors increase the preferential accumulation. Pre-sickling cells (by mixing equal volumes of blood and a 2% solution, weight per volume, of sodium bisulfite dissolved in isotonic saline) after radiolabeling and before washing the cells improve the preferential accumulation further, to approximately 2.6 times.

The highest tumor to normal tissue ratio observed is 4.5, achieved using mouse sickle red blood cells intravenously administered to a recipient mouse with a large mouse tumor. The mouse sickle red blood cells are obtained from a transgenic, knockout mouse engineered in the laboratory of Dr. Raymond Popp (Popp et al. 1997). The mouse tumor is a mammary carcinoma (CSU-Mca) characterized by its large hypoxic fraction, approximately 40%. Image quality, specifically signal to noise, is worse with mouse nuclear medicine imaging due to the small field size and low blood volume compared to the rat.

Figure 4:
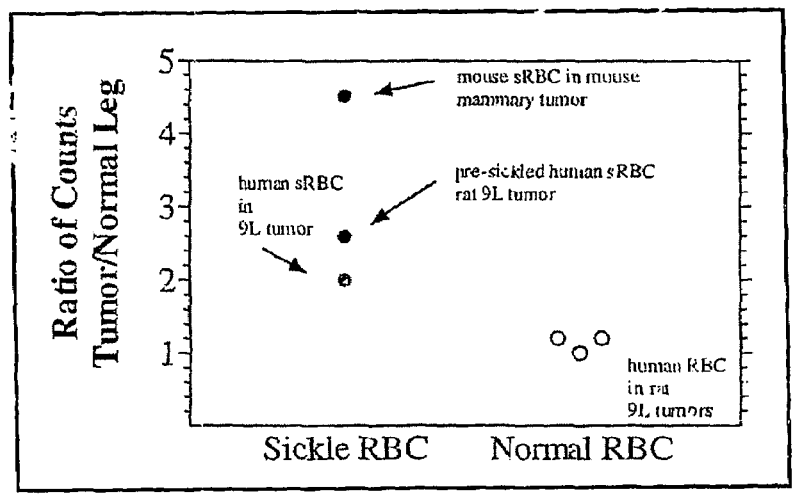
FIG. 4 is a chart summarizing the nuclear medicine experiments, where the ratio of counts in tumor relative to contralateral normal leg between 30 minutes and 60 minutes after intravenous injection of red blood cells.
Figure 5:
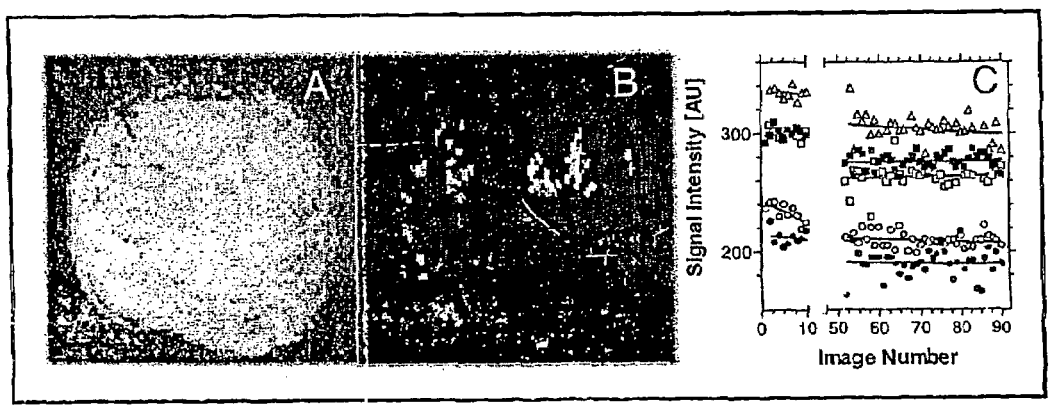
FIG. 5 are images relating to the Nuclear Magnetic Resonance Blood Oxygen Level Dependent or BOLD imaging, where a large 9L rat tumor implanted in the leg was imaged using Blood Oxygen Level Dependent, BOLD imaging where Panel A is a T2* image of a large 9L rat leg tumor before the intravenous infusion of 1 ml of human sickle red blood cells, SRBCs, Panel B are T2* images obtained before the infusion of sRBCs, Panel C illustrates the five largest regions of interest, each with 14 pixels or more, and were within the tumor core, not around the periphery, which accounted for approximately 2% of the tumor pixels (suggesting 2% hypoxia) and the number of pixels in each of the five large ROI were: : ROI 9, 80 pixels; : ROI 3, 75 pixels; : ROI 10, 18 pixels; : ROI 14, 15 pixels; □: ROI 13, 14 pixels.

Control experiments are performed with radiolabeled normal red blood cells intravenously administered to rats with large 9L leg tumors. Tumor to contralateral normal muscle relative activity is only approximately 1.2 between 30 minutes and one hour after the infusion of human normal red blood cells. The results are consistent with the following autoradiographic studies in that sickle cells preferentially aggregate in tumor regions compared with normal tissue. A summary of the nuclear medicine results is given in FIG. 4.

Example Two

Laser Scanning Confocal Microscopy

Figure 6:
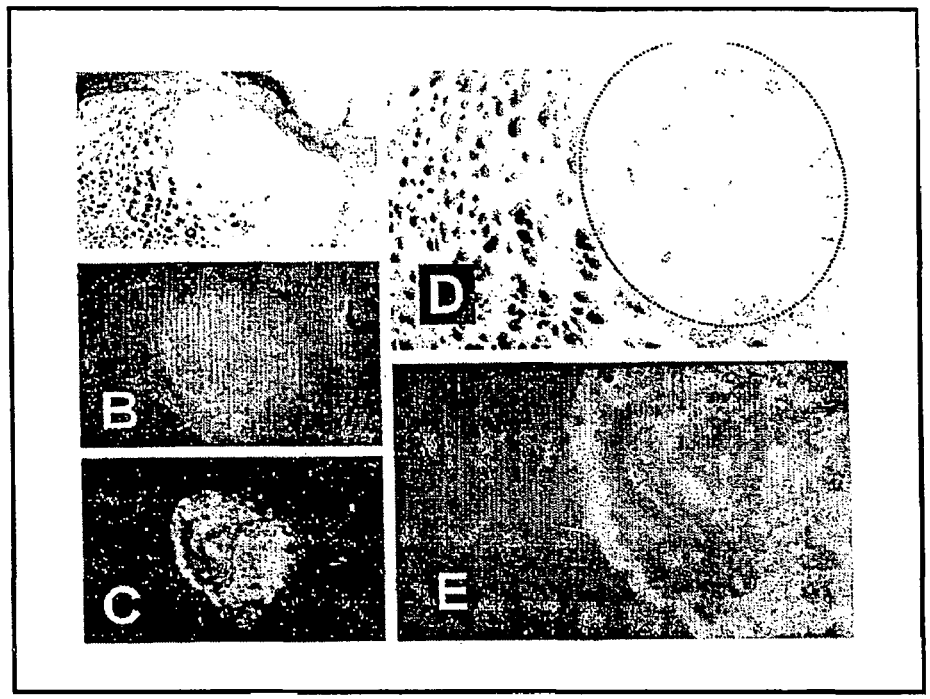
FIG. 6 is a micrograph of a tumor shown through the use of a "conventional" fluorescent microscope following sickle red blood cell delivery, where Panel A is a bright field of the 60 μm thick section, Panel B shows Evans Blue distribution indicating the tumor has leaky vasculature, Panel C illustrates sickle cell localization preferential to the tumor periphery, Panel D and Panel E display magnified views of Panel A and B, wherein the dashed black line in Panel D indicates the approximate tumor boundary.

Preferential aggregation of sickle cells to tumor is observed in rats when sRBC (0.5 ml packed) are labeled with fluorescence (Oregon Green 488 conjugated to a streptavidin-biotin complex that binds to RBC surface proteins (biotinoyl-amino-hexanoic acid, sulfosuccinimidyl ester; Molecular Probes, Inc., Eugene Oreg.) and delivered through the femoral vein one hour before sacrifice. Vasculature is visualized by injecting another fluorescence compound, Evans Blue, which conjugates to albumin in vivo. Evans Blue (2 mls per kg of a 2% w/v solution) is delivered within 10 seconds of sacrificing the rats. Of note is that the distribution of sRBCs within the tumor is not uniform. Some regions, particularly the periphery, sequestered extremely high activity, indicating sickle red blood cells preferentially aggregate to particular regions in a tumor (number of studies, n=9). Congested sRBCs are even visible on bright field (FIG. 6). Normal RBCs did not aggregate in tumor periphery (n=2). There was no red cell congestion in control studies using normal red blood cells. As a consequence of the lack of contrast in the tumor from normal RBCs, similar images as shown in FIG. 6, panel C and E are technically difficult to obtain using normal red cells since exposure times are in the range of hours instead of seconds and at the long exposure times some contrast from Evans Blue is apparent.

Example Three

Autoradiography

Red cells are radiolabeled using the routine clinical kit, Ultra®Tag (Mallinckrodt Medical, Inc., St. Louis, Mo.). Red blood cell aggregation is assessed using $^{99m}$Tc-RBC-autoradiographic technique. $^{99m}$Tc-RBC (30 mCi per rat, 10 mCi per mouse) is intravenously infused over 10 seconds. Arterial blood samples are obtained periodically over the course of the experiment from a femoral artery catheter. Plasma is obtained from these samples by centrifugation to determine untagged activity. The rats are decapitated at the instant the last sample collection is complete, which is approximately 60 minutes after starting the RBC infusion. The exact time of decapitation is carefully measured. The tumors or whole brains are rapidly removed and frozen in 2-methylbutane, cooled to −45° C. with dry ice. The brain then is covered by mounting medium and stored at −80° C.

Radioactivity is determined in the blood and plasma samples by liquid scintillation counting and in tissue by quantitative autoradiography (QAR), coronal sections of brain, each 20 μm thick, is cut in a cryostat set at −17° C., starting at the level of the area postrema and ending at the rostral part of the caudate-putamen. Tumors, 1 mm and larger in diameter are visible during sectioning. Throughout the tumor region, three 10 μm sections adjacent to QAR sections is cut for histological preparation. Sets of sections are to be taken throughout the tissue for autoradiographic and histological preparation. The individual sections are picked up on coverslips and instantly dried on a hot plate at 55° C.

Standards consist of known amounts of Tc-99m mixed vigorously with pureed porcine brain, frozen, cryosectioned and placed next to autoradiographic sections. Those sections designated for autoradiography and a set of standards are placed in cassettes with x-ray film (SB5 or MRM, Kodak, Inc., Rochester, N.Y.). Pairs of sections adjacent to the ones taken for QAR analysis are stained with hematoxylin & eosin (H&E) or histochemical staining (hypoxyprobe-1) for hypoxia examination. After appropriate exposure, the x-ray film is developed and analyzed for radioactivity using an image analysis system (MCID, Image Research, St. Catharines, Ontario, Canada). For each film, the image processing system generates a modified spline fit of the relationship between optical densities and radioactivities from the standards, converts the tissue optical density reading to radioactivity, and produces a color-coded image of tissue radioactivity on a color monitor. Densitometric reading is taken either at several points within each area of interest with a cursor controlled circular reading frame (diameter=300 to 900 μm) or along a "line of interest" with a ladder-like reading frame (see Otsuka et al. 1991, about the latter technique). Because a set of three sections or radiographic images are obtained every 400 μm and most areas of interest appear on several sets of sections, anywhere from 3 (one set of sections) to 12 (4 sets of sections), autoradiographic images are used to evaluate the radioactivity of each area of interest in the tumor center, periphery, adjacent normal tissue, and selected structures in remote, apparently normal structures, if possible. For brain tumors, a matching set of readings is made on the contralateral side.

The individual readings are retained as an indication of heterogeneity within structures and across the tissue and used to obtain a mean value per structure or site of interest. Areas and sites of interest are identified using a stereotactic atlas (Paxinos and Watson 1986) and the adjacent histological sections. (FIG. 1)

Example Four

Nuclear Magnetic Resonance Imaging, Functional Magnetic Resonance Imaging, or BOLD-MRI The terms "functional-MRI," "BOLD-MRI" and t2* images are synonymous. The functional MRI or BOLD MRI pulse sequence used is a T2* weighted sequence termed MUSIC (Loenneker et al. 1996). MUSIC is a T2*-weighted gradient echo sequence that allows for a multi-slice gradient-echo image acquisition in short periods of time. Slice excitations are interleaved, followed by similarly interleaved readouts. This allows for optimally dense signal acquisition in a FLASH sequence with a long T2*-weighted echo time.

Sequence parameters on the 7T system are TE/TR=30/15 ms, FOV=32 mm, matrix size 64×64, flip angle, 0=25 degrees. The sequence acquires data simultaneously from three 2 mm contiguous slices with less than 2 second temporal resolution. One minute before the red blood cell, RBC, infusion, the hypoxia marker is administered intravenously.

Images are acquired in groups of 40, one group before the infusion of red blood cells and several groups after the administration of red cells. A significant decrease in signal in a localized area encompassing several pixels is interpreted as sickle cell aggregation. The 40 pre-RBC images are compared with the post-RBC signal intensity in a pixel-by-pixel basis and using a t-test comparison with a level of significance, p,0.01 two-tailed. A processed image is created that maps pixels that significantly decrease after RBC administration. The signal intensity of the pixel in the processed image is linearly related to the magnitude of the change in signal intensity from the pre-RBC image so regions of RBC aggregation are evident.

After the experiment, the animal is to be sacrificed, frozen, cryosectioned in 10 μm thick slices and processed using the secondary antibody to the hypoxic probe. Immunohistochemical staining is digitized and averaged across 2 mm section of the brain corresponding to the MRI images. Scattergrams of tumor hypoxia digitized from immunohistochemical staining and sickle cell aggregation from BOLD imaging is constructed. Regression analysis is used to determine the correspondence between sickle cell aggregation and immunohistochemically measured hypoxia. An excellent correlation was observed.

This technique demonstrates sickle cell aggregation by employing fast, but low resolution sequences, sensitive, but not wholly dependent on $T_2$ contrast (Loenneker et al. 1996, Robinson et al. 1995). As with other techniques described herein, contrast enhancement is observed in the tumor periphery (n=4). Tumor periphery is not enhanced when normal red cells are used (n=1). Also, enhancement in tumor periphery is abrogated when the animal breathed carbogen, 95% $O_2$, 5% $CO_2$ for 10 minutes (n=1).

Temporal changes in image contrast are exploited to provide single high contrast images reflecting the temporal changes (Cao et al. 1999). Unlike the nuclear medicine data, the regions of relative contrast improve with increasing time in the MR Images (that is, contrast at 1 hour is better than that at 10 minutes, which is better that that at 2 minutes). The interpretation is that the aggregation of cells becomes further deoxygenated with time. The time sequence of BOLD images are amenable to the principle component analysis we have previously applied to change in blood flow (Cao et al. 1999).

Figure 2:
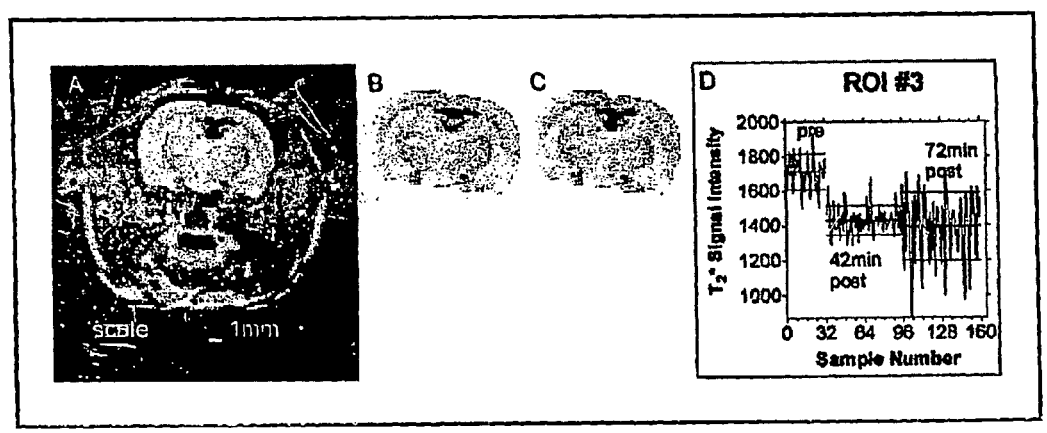
FIG. 2 is a series of images and a chart demonstrating the preferential aggregation of sickle red blood cells in a 9L brain tumor where, Panel A shows a T2-weighted-2 mm slice through the rat head, Panel B replicates the brain region with the evident dark tumor, Panel C shows three regions of interest, ROIs, that had significantly different $T_2^*$ signal intensity before and after 1 ml of human sickle cells were infused intravenously, Panel D illustrates the raw $T_2^*$ signal intensity in arbitrary units for ROI#3, thus, the data herein illustrates that RBCs from patients with sickle cell anemia become deoxygenated (hence the reduced $T_2^*$ signal intensity) and aggregated in the tumor periphery.

The normal tissue and brain tumor are observable in the same image slice through the use of intracranially implanted tumor model (Brown et al. 1999). FIG. 2 also illustrates a BOLD-MRI experiment in the brain of a rat. Following sickle cell delivery, image contrast improved in a few regions that lay on the tumor periphery.

Sickle RBC aggregation in the periphery of a small tumor (<1 mm) is shown using BOLD-MRI. Regarding control experiments, sRBC do not aggregate in normal brain (FIG. 2) and normal RBCs injected to an animal with a tumor do not aggregate preferentially in either normal brain or tumor tissue. To improve resolution, RBCs can be loaded with MRI contrast media such as gadolinium (Gd) and imaged with clinically routine $T_1$ and $T_2$ pulse sequences. Human RBC, 0.5 ml packed, were loaded with Gd and administered intravenously to rats with tumors. Both $T_1$-weighted and $T_2$-weighted contrast is observed, limited to the tumor periphery (n=2, see FIG. 7). In summary, tumor periphery contrast following sickle cell delivery using $T_1$-weighted, $T_2$-weighted, and $T_2$*-weighted imaging was observed.

RBC loading in a hypotonic solution, causing the RBCs to swell and absorb the bathing solution, is superior to loading in a hypertonic solution prior to isotonic solution since a decrease in volume have a tendency to sickle the cells. We use a modification of the procedure described by Johnson et al. (1998) to load red cells with Gd. Briefly, up to 3 mls of RBCs are washed in 50 mls of isotonic saline. Dimethyl-suloxide (DMSO, 2M) is added to the pellet according to the ratio 1:2 for DMSO:RBC. The mixture is agitated and centrifuged. The supernatant is removed and Gd solution (469 mg gadopentetate dimeglumine per ml; Magnevist, Berlex Laboratories, Wayne, N.J. is combined with the RBCs in the ratio 3:1, Gd:RBC. The final mixture is agitated, centrifuged, supernatant removed, and RBCs washed with 50 ml saline three times. Loading of RBCs with Gd occurs because the Gd mixture is hypotonic relative to the RBC loaded with DMSO. DMSO is freely diffusible and, in the three final washes, is diluted from the red cells.

Figure 7:
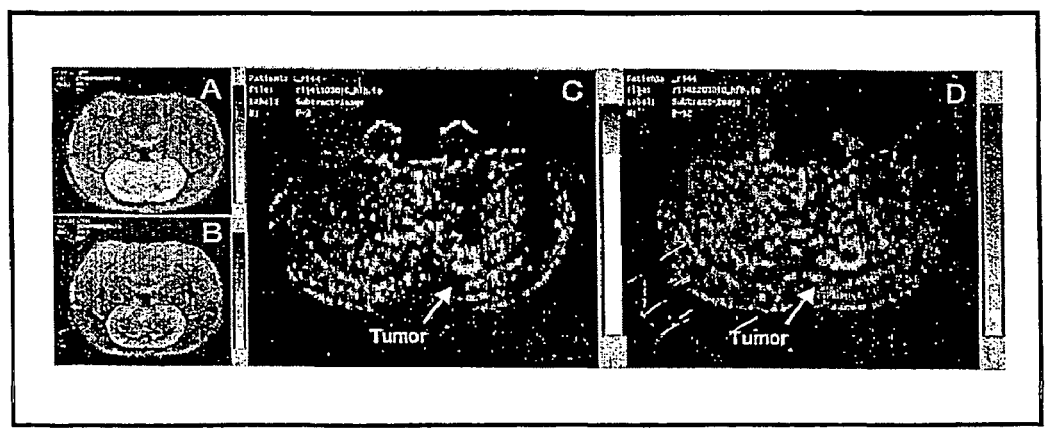
FIG. 7 illustrates 7T MRI coronal images of rat brain with a 1.3 mm diameter tumor, where Panel A and Panel B are $T_1$- and $T_2$-weighted sequences respectively, wherein Panel C and Panel D are magnified views of pre-to-post subtraction images of $T_1$- and $T_2$-weighted sequences respectively.

To improve resolution, red blood cells are doped with contrast agent. Human RBC, 0.5 ml packed, were loaded with Gd-DTPA and administered intravenously to rats with tumors. Both $T_1$-weighted and $T_2$-weighted contrast is observed, limited to the tumor periphery (n=2, see FIG. 7). In summary we have observed tumor periphery contrast following sickle cells delivery using $T_1$-weighted, $T_2$-weighted and $T_2$-weighted imaging. We have not yet optimized the image contrast achievable. (FIG. 7)

The fluorescent microscopy and fMRI data is consistent with the regions of sickle cell accumulation coinciding with tumor hypoxia. Fluorescent labeled sickle cells and tumor hypoxia occur predominantly at the tumor periphery and fMRI, which is sensitive to changes in deoxyhemoglobin, gives evidence that the localization and low oxygen are coincident.

As an alternative method, hypoxyprobe can be administered, while the animal is in the magnet, 15 to 90 minutes before the animal is sacrificed and after sickle cell delivery. The tissue is then excised following MRI, cryosectioned, processed for the hypoxia probe, digitized and three-dimensionally reconstructed to determine the region of hypoxia.

Example Five

Hypoxia Probe

Detection of hypoxia by pimonidazole hydrochloride (hypoxyprobe-1) is utilized. Hypoxyprobe-1 is a commercially available histochemical probe for detecting tissue hypoxia. Available through Natural Pharmacia International Inc. (Belmont, Mass.), hypoxyprobe-1 is a substituted 2-nitroimidazole whose chemical name and only ingredient is pimonidazole hydrochloride. Hypoxyprobe is water soluble (116 mg/mL or 400 millimolar) and stable for at least one year in saline at room temperature. Its plasma halflife in C3H/He mice is 0.5 hrs. Fifteen to 90 minutes after the injection of hypoxyprobe-1, animal is sacrificed, tumor is excised, frozen, cyrosectioned in 10 µm thick sections and allowed to react with the monoclonal antibody that detects protein adducts of hypoxyprobe-1 in hypoxic cells.

As a precaution to avoid hypoxyprobe binding to cells that become hypoxic during animal sacrifice, animals undergo vascular washout by perfusion with heparinized saline as described previously (Kim et al. 1999).

Hypoxyprobe demonstrates a good correlation with sickle cell aggregation. Raleigh et al. (1999) demonstrated good correlation between hypoxyprobe binding and $pO_2$ measured with glass electrodes as well as between hypoxyprobe binding and radiobiological hypoxic fraction. Furthermore, Kavanagh et al. (1999) found a strong correlation between the binding of a different 2-nitroimidazole compound, EF5, and radiobiological hypoxia.

Example Six

Glass Electrodes

Animals are anesthetized with ketamine and xylazine. Mice are secured using a custom jig. Rats are positioned in the stereotactic device using the same coordinates as tumor implantation. For mice, overlaying skin is removed to allow measurement directly in tumor. For rats, the skull burr hole is surgically re-exposed. The glass electrode is attached to the stereotactic needle holder so that it is able to travel into the tumor. For rats, the needle travels down the path of the original needle track. The electrode is advanced with the aid of a micromanipulator. Measurements are made at 50 µm depth increments.

The glass electrodes fabricated on site have several advantages over commercially available probes. The exposed tip is very small, typically 10 µm in diameter. The electrodes have a very rapid response time, approximately half a second, consume only a small amount of oxygen, and are relatively insensitive to "stirring artifacts" (rapid movement of fluid near the tip).

There are several problems with the glass electrode measurement of oxygen, as described by Acker (1989). The probes are invasive, fragile and must be calibrated before and after a tissue measurement. However, despite these problems, they still represent a standard tissue oxygen measurement technique.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Barker P B et al (1999).
2. Bookstein, F. L. (1989).
3. Bristow, R. G., et al (1998).
4. Brix, G. et al (1990).
5. Brizel, D. M. et al (1994).
6. Brown, S. L. et al (1988).
7. Brown, S. L. et al (1999).
8. Cao, Y. et al (1999).
9. Chaplin, D. J. et al (1986).
10. Chaplin, D. J. et al (1995).
11. Chen, C. T. et al (1988).
12. Dewhirst, M. W. (1998).
13. Edzes, H. T. et al (1977).
14. Ewing, J. R. et al (1997).
15. Ewing, J. R. et al (1996).
16. Ewing, J. R. et al (1999).
17. Ewing, J. R. et al (1999)
18. Fyles, A. W. et al (1998).
19. Gatenby, R. A. et al (1988).
20. Grad, J. et al (1990).
21. Grad, J. et al (1990).
22. Kavanagh, M C. et al (1999).
23. Kim, J. H. et al (1999).
24. Kim, J. H. et al (1995).
25. Lartigau, E. et al (1997).
26. Lartigau, E. et al (1993).
27. Leith, J. T. et al (1975).
28. Loenneker, T. et al (1996).
29. Look, D. C. et al (1970).
30. Lew, Y. S. et al (2000).
31. Mason, R. P. et al (1998).
32. Morrison, C. et al (1995).
33. Moulder, J. E. et al (1984).
34. Ordidge, R. J. et al (1991).
35. Paxinos, G. et al (1986).
36. Peck, D. J. et al (1996).
37. Pelizzari, C. A. et al (1989).
38. Popp, R. A. et al (1997).
39. Raleigh, J. A. et al (1998).
40. Raleigh, J. A. et al (1999).
41. Reinhold, H. S. et al (1986).
42. Robinson, S. P. et al (1995).
43. Thomlinson, R H. et al (1955).
44. Trotter, M. J. et al (1989).
45. Wei, L. et al (1998).
46. Wheeler, K. T. et al (1980).
47. Wolff, S. D. et al (1989).
48. Wong, R. K. et al (1997).
49. Young, W. K. et al (1996).
50. Zhang, X. et al (1998).

What is claimed is:

1. A method of diagnosing tumor microenvironment areas characterized by hypoxia, acidosis, and hypertonicity comprising the steps of administering sickle red blood cells to a patient and detecting the location of accumulated sickle red blood cells, whereby the sickle red blood cells accumulate at a tumor microenvironment.

2. The method according to claim 1, wherein said administering step is further defined as administering sickle red blood cells including labels selected from the group consisting of radioactive labels, immunofluorescent tags, Gd, Gd-DTPA, antibodies, compounds, and drugs.

3. The method according to claim 1, wherein said administrating step is further defined as intravenously injecting the sickle red blood cells into a patient.

4. The method according to claim 1, wherein said detecting step is further defined as being selected from the group consisting of magnetic resonance imaging, functional magnetic resonance imaging, nuclear magnetic resonance imaging, autoradiography, laser scanning confocal microscopy, and blood oxygen level dependent imaging.

5. A method of delivering a therapeutic agent to a solid tumor characterized by hypoxia, acidosis, and hypertonicity comprising loading the therapeutic agent into sickle red blood cells and administering the sickle red blood cells including the therapeutic agent into the blood circulation of a patient wherein the sickle red blood cells, including the therapeutic agent, accumulate in the tumor.

6. The method according to claim 5, wherein the therapeutic agent is selected from the group consisting of chemotherapeutic agents, cytostatic chemotherapeutic agents, radiosensitizers, radionuclides, antibodies, anti-inflammatory agents, agents that affect reperfusion injury, adjuvants, and anti-tumor agents.

7. The method according to claim 5, wherein said administering step is further defined as administering intravenously the sickle red blood cells into the patient.

* * * * *

Adverse Decisions in Interference

Patent No. 7,247,501, Jae Ho Kim, Stephen Lawrence Brown and Paul S. Swerdlow, IMAGING AND TARGETING TUMORS USING SICKLE CELLS, Interference No. 105,741, final judgment adverse to the patentees rendered April 22, 2010, as to claims 5-7.

*(Official Gazette, July 27, 2010)*